(12) United States Patent
Yoon et al.

(10) Patent No.: US 10,773,237 B2
(45) Date of Patent: Sep. 15, 2020

(54) METHOD FOR PREPARING SUPER ABSORBENT POLYMER, AND SUPER ABSORBENT POLYMER

(71) Applicant: LG Chem, Ltd., Seoul (KR)

(72) Inventors: Hyung Ki Yoon, Daejeon (KR); Dae Woo Nam, Daejeon (KR); Hyemin Lee, Daejeon (KR); Chang Sun Han, Daejeon (KR); Sung Jong Seo, Daejeon (KR)

(73) Assignee: LG Chem, Ltd. (KR)

( * ) Notice: Subject to any disclaimer, the term of this patent is extended or adjusted under 35 U.S.C. 154(b) by 112 days.

(21) Appl. No.: 15/768,343

(22) PCT Filed: Jan. 3, 2017

(86) PCT No.: PCT/KR2017/000057
§ 371 (c)(1),
(2) Date: Apr. 13, 2018

(87) PCT Pub. No.: WO2017/155197
PCT Pub. Date: Sep. 14, 2017

(65) Prior Publication Data
US 2018/0318793 A1 Nov. 8, 2018

(30) Foreign Application Priority Data

Mar. 11, 2016 (KR) .................. 10-2016-0029834
Aug. 12, 2016 (KR) .................. 10-2016-0103024

(51) Int. Cl.
| | |
|---|---|
| *B01J 20/26* | (2006.01) |
| *C08J 3/24* | (2006.01) |
| *A61L 15/18* | (2006.01) |
| *A61L 15/60* | (2006.01) |
| *B01J 20/32* | (2006.01) |
| *C08F 6/28* | (2006.01) |
| *C08K 9/02* | (2006.01) |
| *C08F 2/44* | (2006.01) |
| *C08F 220/06* | (2006.01) |
| *C08F 2/10* | (2006.01) |
| *A61L 15/24* | (2006.01) |
| *C08F 2/48* | (2006.01) |
| *A61L 15/22* | (2006.01) |
| *B01J 20/10* | (2006.01) |
| *B01J 20/28* | (2006.01) |
| *B01J 20/30* | (2006.01) |
| *C08F 20/06* | (2006.01) |

(52) U.S. Cl.
CPC .............. *B01J 20/267* (2013.01); *A61L 15/18* (2013.01); *A61L 15/225* (2013.01); *A61L 15/24* (2013.01); *A61L 15/60* (2013.01); *B01J 20/103* (2013.01); *B01J 20/28016* (2013.01); *B01J 20/3021* (2013.01); *B01J 20/3085* (2013.01); *B01J 20/321* (2013.01); *B01J 20/3219* (2013.01); *B01J 20/3234* (2013.01); *B01J 20/3293* (2013.01); *C08F 2/10* (2013.01); *C08F 2/44* (2013.01); *C08F 2/48* (2013.01); *C08F 6/28* (2013.01); *C08F 20/06* (2013.01); *C08F 220/06* (2013.01); *C08J 3/245* (2013.01); *C08K 9/02* (2013.01); *C08F 2810/20* (2013.01); *C08J 2333/02* (2013.01); *C08J 2333/08* (2013.01); *C08K 2201/013* (2013.01); *C08K 2201/014* (2013.01)

(58) Field of Classification Search
None
See application file for complete search history.

(56) References Cited

U.S. PATENT DOCUMENTS

| | | | |
|---|---|---|---|
| 5,599,335 A | 2/1997 | Goldman et al. | |
| 7,833,624 B2 | 11/2010 | Harren et al. | |
| 8,466,228 B2 | 6/2013 | Smith et al. | |
| 2002/0128618 A1 | 9/2002 | Frenz et al. | |
| 2006/0073969 A1* | 4/2006 | Torii ................. | A61L 15/60 502/400 |
| 2007/0100304 A1* | 5/2007 | Fell .................. | A61L 15/46 604/359 |
| 2009/0131255 A1 | 5/2009 | Ikeuchi et al. | |
| 2009/0186542 A1 | 7/2009 | Kondo et al. | |
| 2011/0224361 A1 | 9/2011 | Daniel et al. | |
| 2015/0225514 A1 | 8/2015 | Kimura et al. | |
| 2015/0315321 A1* | 11/2015 | Won ................. | A61L 15/22 525/328.8 |
| 2015/0360204 A1 | 12/2015 | Tachi et al. | |

(Continued)

FOREIGN PATENT DOCUMENTS

| | | |
|---|---|---|
| EP | 0629411 A1 | 12/1994 |
| EP | 3345958 A1 | 7/2018 |

(Continued)

OTHER PUBLICATIONS

International Search Report for Application No. PCT/KR2017/000057 dated Apr. 18, 2017.

(Continued)

*Primary Examiner* — Tanisha Diggs
(74) *Attorney, Agent, or Firm* — Lerner, David, Littenberg, Krumholz & Mentlik, LLP

(57) ABSTRACT

The present invention relates to a method for preparing a super absorbent polymer exhibiting improved liquid permeability, gel strength, absorption rate and the like while maintaining excellent absorption performance. The method for preparing the super absorbent polymer comprises the steps of: carrying out a crosslinking polymerization of a water-soluble ethylenically unsaturated monomer having at least partially neutralized acidic groups in the presence of an internal crosslinking agent to form a hydrogel polymer including a cross-linked polymer; drying, pulverizing, and classifying the hydrogel polymer to form a base polymer powder; and surface-crosslinking the base polymer powder by using a surface crosslinking liquid containing a surface crosslinking agent of an alkylene carbonate having 2 to 5 carbon atoms, in the presence of hydrophobic silica particles having a water-contact angle of more than 10° and 150° or less and hydrophilic silica particles having a water-contact angle of 10° or less.

11 Claims, No Drawings

(56) References Cited

U.S. PATENT DOCUMENTS

| | | |
|---|---|---|
| 2016/0214082 A1 | 7/2016 | Lee et al. |
| 2016/0271584 A1 | 9/2016 | Lee et al. |
| 2016/0311985 A1 | 10/2016 | Jung et al. |
| 2017/0015798 A1 | 1/2017 | Lee et al. |
| 2017/0073478 A1 | 3/2017 | Joo et al. |

FOREIGN PATENT DOCUMENTS

| | | | |
|---|---|---|---|
| JP | 2001137704 A | 5/2001 | |
| JP | 3363000 B2 | 1/2003 | |
| JP | 2009270039 A | 11/2009 | |
| JP | 5289955 B2 | 9/2013 | |
| KR | 20150020030 A | 2/2015 | |
| KR | 101507287 B1 | 3/2015 | |
| KR | 20150056572 A | 5/2015 | |
| KR | 101527585 B1 | 6/2015 | |
| KR | 20150067729 A | 6/2015 | |
| KR | 20150113042 A | 10/2015 | |
| KR | 20150143167 A | 12/2015 | |
| KR | 101586383 B1 | 1/2016 | |
| KR | 20160016714 A | 2/2016 | |
| WO | 2004069915 A2 | 8/2004 | |
| WO | 2005027986 A1 | 3/2005 | |
| WO | 2007116777 A1 | 10/2007 | |
| WO | WO-2014178588 A1 * | 11/2014 | ............ C08F 220/06 |

OTHER PUBLICATIONS

Odian, George, "Principle of Polymerization." Second Edition, (Wiley, 1981), p. 203.

Schwalm, Reinhold, "UV Coatings: Basics, Recent Developments and New Applications." Elsevier Science, Dec. 21, 2006, p. 115.

Patent Cooperation Treaty Third Party Observation, dated Aug. 10, 2018 for International Application No. PCT/KR2017/000057, filed Jan. 3, 2017, 10 pages.

Extended European Search Report including Written Opinion for Application No. EP17763460.7 dated Dec. 20, 2018.

* cited by examiner

METHOD FOR PREPARING SUPER ABSORBENT POLYMER, AND SUPER ABSORBENT POLYMER

CROSS-REFERENCE TO RELATED APPLICATION(S)

The present application is a national phase entry under 35 U.S.C. § 371 of International Application No. PCT/KR2017/000057, filed on Jan. 3, 2017, which claims the benefit of Korean Patent Application No. 10-2016-0029834, filed on Mar. 11, 2016, and Korean Patent Application No. 10-2016-0103024, filed on Aug. 12, 2016 with the Korean Intellectual Property Office, the disclosures of which are incorporated herein by reference.

TECHNICAL FIELD

The present invention relates to a super absorbent polymer exhibiting improved liquid permeability, gel strength, absorption rate and the like while maintaining excellent absorption performance, and a preparation method thereof.

BACKGROUND

Super absorbent polymer (SAP) is a synthetic polymer material capable of absorbing moisture from about 500 to about 1,000 times its own weight, and each manufacturer has denominated it as different names such as SAM (Super Absorbency Material), AGM (Absorbent Gel Material) or the like. Such super absorbent polymers started to be practically applied in sanitary products, and now they are widely used for preparation of various products, for example, hygiene products such as paper diapers for children or sanitary napkins, water retaining soil products for gardening, water stop materials for the civil engineering and construction, sheets for raising seedling, fresh-keeping agents for food distribution fields, materials for poultice or the like.

In most cases, these super absorbent polymers have been widely used in the field of hygienic materials such as diapers or sanitary napkins. For these applications, the super absorbent polymer should exhibit a high moisture absorbency, it should not release the absorbed water even in the external pressure, and additionally it should well retain the shape even in a state where the volume is expanded (swelled) by absorbing water, and thereby exhibit excellent liquid permeability.

In particular, in recent years, as studies have been conducted to provide diapers exhibiting excellent performance while having a thinner thickness and a light weight, much attention has been focused on providing a super absorbent polymer having more improved absorption properties such as a liquid permeability and an absorption rate. In order to achieve excellent absorption properties such as a fast absorption rate and improved liquid permeability, it is necessary that the surface strength of the super absorbent polymer particles, particularly the surface cross-linked layer, is made harder and the gel strength is higher. Consequently, it becomes necessary for urine to be evenly and rapidly dispersed in the absorber core of the diaper.

However, in the case where it is desired to increase the gel strength and increase the liquid permeability through a method previously known in the art, there were a drawback that the basic absorption performance (absorbency under no pressure and under pressure) itself is greatly lowered.

Therefore, there is a continuing need to develop a technique capable of providing a super absorbent polymer having improved gel strength, liquid permeability, absorption rate and the like while maintaining excellent basic absorption performance.

Technical Problem

The present invention provides a super absorbent polymer exhibiting improved liquid permeability, gel strength, absorption rate and the like while maintaining excellent absorption performance, and a method for producing the super absorbent polymer.

Technical Solution

The present invention provides a method for preparing a super absorbent polymer comprise the steps of:

carrying out a crosslinking polymerization of a water-soluble ethylenically unsaturated monomer having at least partially neutralized acidic groups in the presence of an internal crosslinking agent to form a hydrogel polymer including a cross-linked polymer;

drying, pulverizing, and classifying the hydrogel polymer to form a base polymer powder; and surface-crosslinking the base polymer powder by using a surface crosslinking liquid containing a surface crosslinking agent of an alkylene carbonate having 2 to 5 carbon atoms, in the presence of hydrophobic silica particles having a water-contact angle of more than 10° and 150° or less and hydrophilic silica particles having a water-contact angle of 10° or less.

The present invention also provides a super absorbent polymer comprising:

a base polymer powder including a first cross-linked polymer of a water-soluble ethylenically unsaturated monomer having at least partially neutralized acidic groups;

a surface cross-linked layer including a second cross-linked polymer formed on the base polymer powder, in which the first cross-linked polymer is further cross-linked via a surface crosslinking agent; and a hydrophilic silica particle that is dispersed on the surface cross-linked layer and has a water-contact angle of 10° or less, wherein the super absorbent polymer has a EFFC represented by the following formula 1 of 24 to 28 g/g, a saline flow conductivity for a physiological saline solution (0.685 wt % sodium chloride aqueous solution) (SFC; (SFC; $\cdot 10^{-7}$ cm$^3\cdot$ s/g) of 85 to 160 ($\cdot 10^{-7}$cm$^3\cdot$ s/g), and a gel strength (G') of 9,000 to 15,000 Pa.

$$EFFC=(CRC+AUP)/2 \qquad \text{[Formula 1]}$$

in the formula 1,

CRC represents a centrifuge retention capacity for a physiological saline solution (0.9 wt % sodium chloride aqueous solution) of the super absorbent polymer for 30 minutes, AUP represents an absorbency under pressure under 0.7 psi for a physiological saline solution (0.9 wt % sodium chloride aqueous solution) of the super absorbent polymer for 1 hour.

the gel strength (G') represents a horizontal gel strength of the super absorbent polymer measured using a rheometer, after absorbing and swelling a physiological saline solution (0.9 wt % sodium chloride aqueous solution) to the super absorbent polymer for 1 hour.

Hereinafter, the super absorbent polymer according to specific embodiments of the invention, the preparation method thereof, and the like will be described in more detail. However, they are merely presented as an example of the present invention, and will be apparent to those skilled in the art that the scope of the present invention is not limited to these embodiments, and various modifications can be made according to the embodiments within the scope of the present invention.

In addition, unless stated otherwise throughout this specification, the term "comprises" or "contains" means to include any constituent element (or constituent component) without particular limitation, and it cannot be interpreted as a meaning of excluding an addition of other constituent element (or constituent component).

According to one embodiment of the present invention, there is provided a method for preparing a super absorbent polymer comprise the steps of:

carrying out a crosslinking polymerization of water-soluble ethylenically unsaturated monomer having at least partially neutralized acidic groups in the presence of an internal crosslinking agent to form a hydrogel polymer including a cross-linked polymer;

drying, pulverizing, and classifying the hydrogel polymer to form a base polymer powder; and surface-crosslinking the base polymer powder by using a surface crosslinking liquid containing a surface crosslinking agent of an alkylene carbonate having 2 to 5 carbon atoms, in the presence of hydrophobic silica particles having a water-contact angle of more than 10° and 150° or less and hydrophilic silica particles having a water-contact angle of 10° or less.

The present inventors have conducted researches to further improve a gel strength, a liquid permeability and an absorption rate of the super absorbent polymer. As a result, the inventors have found that, as the base polymer powder having high gel strength is obtained by optimizing the conditions of the production process of the super absorbent polymer, for example, type and content of an internal crosslinking agent and the polymerization conditions to be described later, and the surface crosslinking proceeds under specific surface crosslinking conditions (for example, specific silica particles, more specifically, two or more hydrophilic and hydrophobic silica particles are used simultaneously or separately during surface crosslinking, etc.), it is possible to provide a super absorbent polymer which maintains excellent absorption performance (absorbency under no pressure and under pressure; CRC, AUP and EFFC to be described later) while greatly improving a gel strength, a liquid permeability and an absorption rate compared to those previously known.

Particularly, as specific silica particles defined in a predetermined contact angle range are used at the time of surface crosslinking and the surface crosslinking progresses under a constant temperature elevation condition or the like, it is thought that the surface cross-linked layer having a certain level or more of thickness can be evenly formed on the base polymer powder having high gel strength. This is presumably because the specific silica particles are uniformly contained in the cross-linked structure of the surface cross-linked layer, thereby further tightening the cross-linked structure, and also the surface crosslinking reaction appropriately occurs around the respective silica particles under the above temperature elevation condition at the time of surface crosslinking, thereby forming a proper cross-linked structure.

Thus, since the surface cross-linked layer can further increase the gel strength of each of the super absorbent polymer particles, the super absorbent polymer of one embodiment can exhibit high gel strength, greatly improve a SFC and a liquid permeability, and thus improve an absorption rate. In addition, as the internal cross-linked structure and the surface cross-linked structure of the super absorbent polymer prepared by the method of one embodiment is optimized, it is possible to maintain excellent absorption performance defined by a relatively high EFFC (arithmetic average value of CRC and AUP).

Thus, the super absorbent polymer of one embodiment exhibits significantly improved liquid permeability, gel strength and absorption rate as well as superior absorption performance than those previously known, and thus can be very preferably applied to various sanitary materials such as ultra-thin type diapers with a content of pulp decreased.

Hereinafter, a method for producing a super absorbent polymer of one embodiment will be described in more detail.

Typically, the super absorbent polymer can be prepared by polymerizing a water-soluble ethylenically unsaturated monomer having at least partially neutralized acidic groups, such as a mixture of acrylic acid and its sodium salt in which at least a part of carboxylic acid is neutralized with sodium salt, in the presence of an internal crosslinking agent, and then drying, pulverizing and classifying the resultant, followed by surface crosslinking. In a specific example, in the preparation method of one embodiment, the super absorbent polymer can be obtained by carrying out a crosslinking polymerization of the above-mentioned monomer in the presence of an internal cross-linking agent to obtain a base polymer powder, and then surface-crosslinking the base polymer powder in the presence of a predetermined surface crosslinking agent and hydrophobic and hydrophilic silica particles.

In particular, it has been found that, as the base polymer powder having high gel strength is obtained by adjusting the type and content of an internal crosslinking agent, the polymerization conditions, and the like, for example, as the surface crosslinking proceeds using specific silica particles, more specifically hydrophilic and hydrophobic silica particles defined by a range of contact angle of water, it is possible to prepare a super absorbent polymer exhibiting the above-mentioned physical properties and effects. In a preferable example, in the preparation method of one embodiment, specifically the hydrophilic silica particles described below, more specifically the hydrophilic and hydrophobic silica particles described below can be used at the time of surface crosslinking.

First, in the preparation method of this embodiment, the hydrophobic silica particles having a water-contact angle of more than 10°, or more than 10° and 150° or less, more preferably 12° to 150°, and the hydrophilic silica particles having a water-contact angle of 10° or less, or 1 to 10° can be used at the time of surface crosslinking. Thus, the super absorbent polymer produced by the method of one embodiment may further include hydrophilic silica particles and/or hydrophobic silica particles dispersed on the surface of the base polymer powder, for example, on the surface cross-linked layer.

In this case, "the hydrophilic silica particles or the hydrophobic silica particles are dispersed on the surface cross-linked layer" may mean that these respective silica particles are contained/dispersed in the cross-linked structure of the surface cross-linked layer, or are embedded in the surface of the surface cross-linked layer.

Meanwhile, in a specific example, the hydrophobic silica particles may be contained and treated in a surface cross-linking liquid, or may be separately mixed and treated on the base polymer powder before surface crosslinking, as described in more detail below. Thus, such hydrophobic silica particles, for example, at least a part thereof, may be present on the surface of the base polymer powder, for example, in the surface cross-linked layer, and a part thereof may be present in a state of being embedded in the surface of the base polymer powder. In addition, the hydrophilic silica particles may be dispersed on the surface cross-linked layer, and the hydrophilic silica particles may be present in the cross-linked structure contained therein, or a part thereof may be present in a state of being embedded in the surface of the base polymer powder.

As the hydrophobic and hydrophilic silica particles are treated in the above-described manner, these hydrophilic and/or hydrophobic silica particles can effectively surround the surface crosslinking liquid. For these reasons, it is possible to prevent the surface crosslinking liquid from locally absorbing only a part of the base polymer powder quickly, and it can be uniformly coated over the entire surface of the base polymer powder. Thus, the surface crosslinking can be performed uniformly, and these silica particles can also be evenly distributed on the surface cross-linked layer.

As described above, the hydrophilic and/or hydrophobic silica particles for improving the liquid permeability are present at least on the surface cross-linking layer, the surface crosslinking liquid is evenly coated and thus the surface cross-linking is evenly performed on the base polymer powder. Thereby, excellent physical properties such as improved liquid permeability can be expressed and maintained for a long period of time.

As the hydrophobic silica particles, one or more of the commercially available hydrophobic silica particles having the contact angle range described above can be used without any particular limitation. More suitably, when the hydrophobic silica particles are incorporated in the surface cross-linking liquid, particles having a contact angle of more than 10° and 50° or less can be used, or particles having a contact angle of 50° to 150° or less can be used together with a separate dispersant in terms of dispersibility in a surface crosslinking liquid or the like.

When the hydrophobic silica particles are treated by separately adding and mixing the same with the base polymer powder before the surface crosslinking, the particles having a contact angle of 50° to 150° or less can be more preferably used from the viewpoint of more effective liquid permeability and improvement in absorption rate. In addition, as the above-mentioned hydrophilic silica particles, one or more of the commercially available water-dispersible silica particles having a contact angle range of 10° or less can be used without any particular limitation.

More specifically, for the hydrophobic silica particles, hydrophobic silica particles available under trade name: DM30S, Aerosil or the like can be suitably used. As the hydrophilic silica particles, water-dispersible silica particles available under trade name: ST-O or ST-AK, etc. may be suitably used, thereby further improving the liquid permeability, the absorption rate and the like of the super absorbent polymer.

The water-contact angle, which distinguishes the hydrophilic and hydrophobic silica particles from each other, can be defined as a water-contact angle of each silica particle measured on a glass substrate.

On the other hand, in the method for preparing a super absorbent polymer of one embodiment, the water-soluble ethylenically unsaturated monomer may include at least one selected from the group consisting of anionic monomers of acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid or 2-(meth)acrylamido-2-methylpropanesulfonic acid, and their salts; non-ionic, hydrophilic group-containing monomers of (meth)acrylamide, N-substituted (meth)acrylate, 2-hydroxyethyl(meth)acrylate, 2-hydroxypropyl(meth)acrylate, methoxypolyethylene glycol (meth)acrylate or polyethylene glycol (meth)acrylate; and amino group-containing unsaturated monomers of (N,N)-dimethylaminoethyl(meth)acrylate or (N,N)-dimethylaminopropyl(meth)acrylamide, and their quaternary product. Among them, acrylic acid and/or a salt thereof, for example, an alkali metal salt of acrylic acid or and/or a sodium salt thereof having at least partially neutralized acrylic acids can be used, and the use of these monomers enables production of a super absorbent polymer having more excellent physical properties. In the case of using acrylic acid and its alkali metal salt as a monomer, it is possible to use acrylic acid after neutralizing at least a part thereof with a basic compound such as caustic soda (NaOH).

The internal crosslinking agent for crosslinking the monomer may include bis(meth)acrylamide having 8 to 12 carbon atoms, poly(meth)acrylate of polyol having 2 to 10 carbon atoms and poly(meth)acrylate having 2 to 10 carbon atoms. More specifically, for the internal crosslinking agent, one or more poly(meth)acrylates of polyols selected from the group consisting of polyethylene glycol di(meth)acrylate, polypropyleneoxy di(meth)acrylate, glycerin diacrylate, glycerin triacrylate and trimethylol triacrylate can be suitably used. Among them, as an internal crosslinking agent such as polyethylene glycol di(meth)acrylate is used, the internal crosslinking structure is optimized and a base polymer powder or the like having high gel strength can be obtained, Thereby, the super absorbent polymer satisfying excellent physical properties can be more appropriately obtained.

The specific certain internal crosslinking agent can be used in a ratio of about 0.005 mol or more, or about 0.005 to 0.1 mol, or about 0.005 to 0.05 mol (or about 0.3 or more parts by weight, or 0.3 to 0.6 parts by weight relative to 100 parts by weight of acrylic acid), based on 1 mol of non-neutralized acrylic acid contained in the monomer. The base polymer powder having a high gel strength before surface crosslinking can be suitably obtained according to the range of the content of the internal crosslinking agent, and a super absorbent polymer having excellent physical properties can be obtained through the method of one embodiment.

After carrying out a crosslinking polymerization of the monomer using the internal crosslinking agent, processes such as drying, pulverizing and classifying are performed to obtain a base polymer powder. Through the processes such as the pulverizing and classifying, the base polymer powder and the super absorbent polymer obtained therefrom are suitably prepared and provided so as to have a particle size of about 150 to 850 µm. More specifically, at least about 95% by weight of the base polymer powder and the super absorbent polymer obtained therefrom have a particle size of about 150 to 850 µm, and fine particles having a particle size of less than about 150 µm can be less than about 3% by weight, or less than about 1.5% by weight.

By adjusting the particle size distribution of the base polymer powder and the super absorbent polymer within the preferred range, the super absorbent polymer can more appropriately exhibit the physical properties already mentioned above.

On the other hand, hereinafter, the method of one embodiment described above will be described in more detail according to respective steps. However, with regard to the monomers, internal crosslinking agent, silica particles and particle size distribution already described above, duplicating explanation thereon will be omitted, and the remaining process configuration and condition will be described in detail according each step of the process.

The method for preparing the super absorbent polymer may comprise the steps of: forming a hydrogel polymer by carrying out a thermal polymerization or photo polymerization of a monomer composition including a water-soluble ethylenically unsaturated monomer, an internal crosslinking agent and a polymerization initiator; drying the hydrogel polymer; pulverizing and classifying the dried polymer to form a base polymer powder; and surface-crosslinking the base polymer powder using a surface crosslinking liquid including a surface crosslinking agent of an alkylene carbonate having 2 to 5 carbon atoms in the presence of the hydrophobic and hydrophilic silica particles In the above preparation method, the monomer composition includes a water-soluble ethylenically unsaturated monomer, an internal crosslinking agent and a polymerization initiator, and the types of the monomers are the same as those already described above.

Further, in the above composition, the concentration of the water-soluble ethylenically unsaturated monomer may be 20 to 60% by weight, or 40 to 50% by weight based on the entire monomer composition including the respective raw materials and solvents described above, and it may be controlled to be an adequate concentration in consideration of the polymerization time, the reaction conditions or the like. However, when the concentration of the monomer is too low, the yield of the super absorbent polymer is low and there may be a problem with economics. By contrast, when the concentration is too high, there may be problems on the process that some of the monomers may be deposited or the pulverizing efficiency of the prepared hydrogel polymer appears to be low in the pulverizing process, and thus the physical properties of the super absorbent polymer may decrease.

Further, the polymerization initiator is not particularly limited as long as it is what is generally used in the preparation of the super absorbent polymer.

Specifically, the polymerization initiator may include a thermal polymerization initiator or a photo polymerization initiator by UV irradiation, according to the polymerization method. However, even in the case of photo polymerization method, a thermal polymerization initiator may be additionally included because a certain amount of heat is generated by the irradiation of UV ray and the like and a certain amount of heat is generated according to the progress of the exothermic polymerization reaction.

The photo polymerization initiator can be used without limitation in the constitution as long as it is a compound which can form a radical by a light such as an UV ray.

The photo polymerization initiator used herein may include, for example, one or more initiators selected from the group consisting of a benzoin ether, a dialkyl acetophenone, a hydroxyl alkylketone, a phenyl glyoxylate, a benzyl dimethyl ketal, an acyl phosphine, and a a-aminoketone. Meanwhile, as the specific example of the acyl phosphine, commercialized lucirin TPO, namely, 2,4,6-trimethyl-benzoyl-trimethyl phosphine oxide may be used. More various photo polymerization initiators are well disclosed in "UV Coatings: Basics, Recent Developments and New Application" written by Reinhold Schwalm, (Elsevier, 2007), p 115, however the example of the photo polymerization initiator is not limited thereto.

The photo polymerization initiator may be included in the concentration of 0.01% to 1.0% by weight based on the monomer composition. When the concentration of the photo polymerization initiator is too low, the polymerization rate may become slow, and when the concentration of the photo polymerization initiator is too high, the molecular weight of the super absorbent polymer becomes small and the physical properties may become uneven.

And, as the thermal polymerization initiator, one or more selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), and the like; and examples of the azo-based initiator include 2,2-azobis(2-amidinopropane) dihydrochloride, 2,2-azobis-(N,N-dimethylene)isobutyramidine dihydrochloride, 2-(carbamoylazo)isobutylonitril, 2,2-azobis[2-(2-imidazolin-2-yl)propane]dihydrochloride, 4,4-azobis-(4-cyanovaleric acid) or the like. More various thermal polymerization initiators are well disclosed in "Principle of Polymerization" written by Odian, (Wiley, 1981), p 203, however the example of the thermal polymerization initiator is not limited thereto.

The thermal polymerization initiator may be included in the concentration of 0.001% to 0.5% by weight based on the monomer composition. When the concentration of the thermal polymerization initiator is too low, the additional thermal polymerization hardly occurs and the effect resulting from the addition of the thermal polymerization initiator may be poor, and when the concentration of the thermal polymerization initiator is too high, the molecular weight of the super absorbent polymer becomes small and the physical properties may become uneven.

In addition, the types of the internal crosslinking agent contained together with the monomer composition are the same as those already described above. Such internal crosslinking agent may be included in a concentration of 0.01% to 0.5% by weight based on the monomer composition and thus can cross-link the prepared polymer. Further, as already described above, the internal crosslinking agent can be used in a ratio of 0.005 mol or more, or 0.005 to 0.1 mol, or 0.005 to 0.05 mol (or 0.3 or more parts by weight, or 0.3 to 0.6 parts by weight relative to 100 parts by weight of acrylic acid), based on 1 mol of non-neutralized acrylic acid contained in the internal crosslinking agent. As the internal crosslinking agent is used within such content range, a high gel strength of the base resin powder can be suitably attained. By using the above, the super absorbent polymer more suitably satisfying the physical properties according to one embodiment can be obtained.

In addition, the monomer composition may further include additives such as a thickener, a plasticizer, a preservation stabilizer, an antioxidant, and so on, as needed.

The monomer composition may be prepared in the form of solution wherein the raw materials such as the water-soluble ethylenically unsaturated monomer, the photo polymerization initiator, the thermal polymerization initiator, the internal crosslinking agent, and the additives are dissolved in a solvent.

At this time, the above-described solvents can be used without limitation in the constitution as long as they are those which can dissolve said components. For example, one or more solvents selected from the group consisting of water, ethanol, ethyleneglycol, diethyleneglycol, triethyleneglycol, 1,4-butanediol, propyleneglycol, ethyleneglycol monobutylether, propyleneglycol monomethylether, propyleneglycol monomethylether acetate, methylethylketone, acetone, methylamylketone, cyclohexanone, cyclopentanone, diethyleneglycol monomethylether, diethyleneglycol ethylether, toluene, xylene, butylolactone, carbitol, methylcellosolve acetate, and N,N-dimethyl acetamide, and so on may be used alone or in combination.

The solvent may be included in the residual quantity excluding the components disclosed above based on the total content of the monomer composition.

Meanwhile, the method of forming a hydrogel polymer by subjecting such monomer composition to the thermal polymerization or photo polymerization can be used without limitation in the constitution as long as it is a method generally used in the polymerization.

Specifically, the polymerization method is largely classified into the thermal polymerization and the photo polymerization according to the polymerization energy source. Usually, the thermal polymerization may be carried out in the reactor like kneader equipped with agitating spindles, and the photo polymerization may be carried out in the reactor equipped with movable conveyor belt, however the polymerization methods disclosed above are just the examples, and the present invention is not limited to the polymerization methods disclosed above.

As an example, the hydrogel polymer obtained by subjecting to the thermal polymerization in the reactor like kneader equipped with the agitating spindles disclosed above by providing hot air thereto or heating the reactor may have the size of centimeters or millimeters when it is discharged from the outlet of the reactor, according to the types of the agitating spindles equipped in the reactor. Specifically, the size of the obtained hydrogel polymer can be variously shown according to the concentration of the monomer composition fed thereto, the feeding speed, and the like, and the hydrogel polymer of which the weight average particle size is 2 to 50 mm can be generally obtained.

Further, as described above, when the photo polymerization is carried out in a reactor equipped with a movable conveyor belt, the hydrogel polymer typically obtained may be a hydrogel polymer in a sheet-type having a width of the belt. In this case, the thickness of the polymer sheet may vary according to the concentration of the monomer composition fed thereto and the feeding speed, and the polymer sheet is preferably controlled to have a thickness of 0.5 to 5 cm. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the thickness of the polymer due to the excessively high thickness.

In this case, the hydrogel polymer thus obtained by the method may have typically a water content of 40 to 80% by weight. Meanwhile, the term "water content" as used herein means a weight occupied by moisture with respect to a total amount of the hydrogel polymer, which may be the value obtained by subtracting the weight of the dried polymer from the weight of the hydrogel polymer. Specifically, the water content is defined as a value calculated by measuring the weight loss according to evaporation of water in the polymer during the drying process of increasing the temperature of the polymer with infrared heating. At this time, the water content is measured under the drying conditions which are determined as follows; the temperature is increased from room temperature to 180° C., then the temperature is maintained at 180° C., and the total drying time is set to 20 minutes, including 5 minutes for the temperature rising step.

Next, the step of drying the hydrogel polymer thus obtained is performed.

If necessary, a coarsely pulverizing step may be performed before the drying step, in order to increase the efficiency of the drying step.

In this case, a pulverizing device used herein may include, but the constitution is not limited to, any one selected from the group consisting of a vertical pulverizing device, a turbo cutter, a turbo grinder, a rotary cutter mill, a cutter mill, a disc mill, a shred crusher, a crusher, a chopper, and a disc cutter, but is not limited thereto.

In this case, the coarsely pulverizing step may be performed so that the hydrogel polymer has a particle size of 2 to 15 mm.

To pulverize the polymer to have a particle size of less than 2 mm is technically not easy due to a high water content of the hydrogel polymer, and a phenomenon of agglomeration may occur between the pulverized particles. Meanwhile, if the polymer is pulverized to have a particle size of larger than 15 mm, the effect of increasing the efficiency in the subsequent drying step may be insignificant.

The hydrogel polymer coarsely pulverized as above or immediately after polymerization without the coarsely pulverizing step is subjected to a drying step. At this time, the drying temperature of the drying step may be 150 to 250° C. When the drying temperature is less than 150° C., there is a concern that the drying time becomes excessively long or the physical properties of the super absorbent polymer finally formed may be deteriorated, and when the drying temperature is higher than 250° C., only the surface of the polymer is excessively dried, and thus there is a concern that fine powder may be generated during the subsequent pulverization process and the physical properties of the super absorbent polymer finally formed may be deteriorated. Therefore, the drying process may be preferably performed at a temperature of 150 to 200° C., and more preferably 160 to 180° C.

Meanwhile, the drying step may be carried out for 20 to 90 minutes, in consideration of the process efficiency, but is not limited thereto.

Furthermore, any known drying method may be selected and used in the drying step without limitation in the constitution if it can be generally used for drying the hydrogel polymer. Specifically, the drying step may be carried out by a method of supplying hot air, irradiating infrared rays, irradiating microwaves, irradiating ultraviolet rays or the like. When the drying step as above is finished, the water content of the polymer may be 0.1 to 10% by weight.

Next, the dried polymer obtained from the drying step is subjected to a pulverization step.

The polymer powder obtained from the pulverization step may have a particle size of 150 to 850 µm. Specific examples of a milling device that can be used to achieve the above particle size may include a pin mill, a hammer mill, a screw mill, a roll mill, a disc mill, a jog mill or the like, but the present invention is not limited thereto.

In order to properly control the physical properties of the super absorbent polymer powder finally manufactured after the pulverization step, a separate classifying step can be performed according to the particle sizes of the polymer powders obtained from the pulverization. Preferably, a polymer having a particle size of 150 to 850 µm is classified and only particle having such particle size is subjected to the surface crosslinking reaction and finally, it is commercialized. The particle size distribution of the base polymer powder obtained through such process has been described above, and thus more specific description thereon will be omitted.

On the other hand, after obtaining the base polymer powder through the pulverizing and classifying steps, the super absorbent polymer can be prepared through the surface crosslinking step. The types of the hydrophilic and/or hydrophobic silica particles usable in the surface crosslinking step have been described above, and thus more specific description thereon will be omitted.

In such surface crosslinking step, in one example, a method in which the base polymer powder is subjected to heat treatment in the presence of the hydrophobic silica particles, the hydrophilic silica particles, and the surface crosslinking liquid containing the surface crosslinking agent to carry out a surface crosslinking the surface can be used, but in another example, a method in which, after mixing and adding hydrophobic silica particles to the base polymer powder, the base polymer powder is subjected to heat treatment in the presence of the hydrophilic silica particles and the surface crosslinking liquid containing the surface crosslinking agent to carry out a surface crosslinking the surface can be used.

In addition, in the method according to the above example, in order to use hydrophobic silica particles in a form of being appropriately dispersed in the surface crosslinking liquid, particles having a contact angle of more than 10° and 50° or less (that is, silica particles showing relatively small hydrophobicity) can be used, or particles having a contact angle of 50° to 150° or less can be used together with another dispersant. As the dispersing agent, any dispersant which has been used for dispersing hydrophobic silica particles in a polar solvent such as a water solvent can be used without any particular limitation, and for example, Tween type dispersant, Span type dispersant, polysaccharide type dispersant or the like can be used.

In another method of separately treating the hydrophobic silica particles, the hydrophobic silica particles may be mixed in a solid state with the base polymer powder to carry out a dry surface treatment, and the treatment method thereof may be based on a dry treatment and/or a mixing method of a general inorganic powder.

The hydrophobic silica particles and the hydrophilic silica particles may be used in an amount of 0.0001 to 0.3 parts by weight, or 0.001 to 0.1 parts by weight, based on 100 parts by weight of the base polymer powder, respectively. Thus, the liquid permeability and absorption rate of the super absorbent polymer can be improved more effectively according to the use of the respective silica particles.

With regard to the method of adding the surface crosslinking liquid containing the hydrophilic silica particles, the surface crosslinking agent and optionally the hydrophobic silica particles to the base polymer powder, there is no limitation in the constitution. For example, a method of adding and mixing the surface crosslinking liquid and the base polymer powder in a reactor, a method of spraying the surface crosslinking liquid onto the base polymer powder, or a method of continuously feeding the base polymer powder and the surface crosslinking liquid to a mixer which is continuously operated, or the like, may be used.

Further, more suitable examples of the alkylene carbonate having 2 to 5 carbon atoms that can be used as the surface crosslinking agent in the surface crosslinking step include ethylene carbonate, propylene carbonate, and butylene carbonate. Among them, it is also possible to use two or more of them together.

The surface crosslinking liquid may further contain a polycarboxylic acid-based copolymer disclosed in Korean Patent Laid-Open Publication No. 2015-0143167 (Korean Patent Application No. 2014-0072343), and these copolymers can be contained in the surface crosslinking liquid in the content of 0.01 to 0.1 pars by weight based on 100 parts by weight of the base polymer powder. Due to the use of these specific surface crosslinking liquids, excellent particle strength, liquid permeability and absorption performance of one embodiment can be more effectively achieved.

In addition, the surface crosslinking liquid may further include water and/or methanol as a medium. Thus, there is an advantage that the surface crosslinking agent and the silica particles can be evenly dispersed on the base polymer powder. In this case, the content of water and methanol can be applied by adjusting the addition rate with respect to 100 parts by weight of the base polymer powder, for the purpose of inducing the uniform dispersion of the surface crosslinking agent and the silica particles, preventing the phenomenon of aggregation of the base polymer powder and at the same time optimizing the surface penetration depth of the surface crosslinking agent.

Meanwhile, in the surface crosslinking step, the surface crosslinking reaction can be proceeded by heating the surface crosslinking liquid-added base polymer powder at a maximum reaction temperature of 140° C. to 200° C., or 150° C. to 190° C. for 5 minutes to 80 minutes, or 10 minutes to 70 minutes, or 20 minutes to 65 minutes. More specifically, the surface crosslinking step can be proceeded by subjecting to a heat treatment under the conditions in which the temperature is raised from an initial temperature of 20° C. to 130° C., or 40° C. to 120° C. to the maximum reaction temperature for 10 minutes to 40 minutes, and the maximum temperature is maintained for 5 minutes to 80 minutes.

By satisfying the conditions of such a surface crosslinking step (in particular, the temperature elevation conditions and the reaction conditions at the maximum temperature of the reaction), the super absorbent polymer suitably satisfying excellent liquid permeability and absorption rate can be prepared.

A means for raising the temperature for surface crosslinking reaction is not particularly limited. Heating may be performed by providing a heating medium or by directly providing a heat source. In this case, the type of the heating medium applicable herein may be a hot fluid such as steam, hot air, hot oil, or the like, but the present invention is not limited thereto. Further, the temperature of the heating medium provided may be properly controlled, considering the means of the heating medium, the heating rate, and the target temperature. Meanwhile, as the heat source provided directly, an electric heater or a gas heater may be used, but the present invention is not limited to these examples.

Meantime, the super absorbent polymer prepared by the preparation method described above may comprise a base polymer powder including a first cross-linked polymer of a water-soluble ethylenically unsaturated monomer having at least partially neutralized acidic groups; a surface cross-linked layer including a second cross-linked polymer formed on the base polymer powder, in which the first cross-linked polymer is further cross-linked via a surface crosslinking agent; and a hydrophilic silica particle that is dispersed on the surface cross-linked layer and has a water-contact angle of 10° or less. Such super absorbent polymer may further comprise hydrophobic silica particles that are dispersed on the surface cross-linked layer and have a water-contact angle of more than 10° and 150° or less.

Further, as already described above, the hydrophilic and/or hydrophobic silica particles may be dispersed in the cross-linked structure in the surface cross-linked layer or may be present in a state of being embedded in the surface of the surface cross-linked layer.

In such super absorbent polymer, hydrophilic and/or hydrophobic silica particles are used at the time of surface crosslinking, the base polymer powder is produced under the above-mentioned predetermined conditions, and the surface crosslinking step proceeds. Thereby, it has a form in which hydrophilic and/or hydrophobic silica particles are uniformly dispersed on the surface cross-linked layer, and furthermore exhibits excellent absorption performance together with more improved liquid permeability, gel strength and absorption rate. Various physical properties of the super absorbent polymer can be defined by the respective physical property values described later.

First, the super absorbent polymer may have a centrifuge retention capacity (CRC) of 25 to 35 g/g, or 26 to 31 g/g. Thus, the super absorbent polymer prepared by the method of one embodiment can exhibit excellent absorbency under no pressure.

In this case, the centrifuge retention capacity (CRC) for the physiological saline solution can be calculated by the following calculation equation 1 after absorbing the super absorbent polymer in a physiological saline solution over a period of 30 minutes.

$$CRC(g/g) = \{[W_2(g) - W_1(g) - W_0(g)]/W_0(g)\} \quad \text{[Calculation Equation 1]}$$

in the calculation equation 1, $W_0(g)$ is an initial weight(g) of the super absorbent polymer, $W_1(g)$ is a weight of the device not including the super absorbent polymer, measured after soaking the same in a physiological saline solution for 30 minutes and dehydrating the same by using a centrifuge at 250 G for 3 minutes, and $W_2(g)$ is the weight of the device including the super absorbent polymer, measured after soaking the same in a physiological saline solution at room temperature for 30 minutes, and then dehydrating the same by using a centrifuge at 250 G for 3 minutes.

Further, the super absorbent polymer may have an absorbency under pressure (AUP) of 24 to 30 g/g, or 24.2 to 27 g/g. As described above, the super absorbent polymer can exhibit excellent absorbency even under pressure.

The absorbency under pressure (AUP) can be calculated by the following calculation equation 2 after absorbing the super absorbent polymer in a physiological saline solution under pressure of 0.7 psi over a period of 1 hour.

$$AUP(g/g) = [W_4(g) - W_3(g)]/W_0(g) \quad \text{[Calculation Equation 2]}$$

in the calculation equation 2, $W_0(g)$ is an initial weight(g) of the super absorbent polymer, $W_3(g)$ is the total sum of a weight of the super absorbent polymer and a weight of the device capable of providing a load to the super absorbent polymer, and $W_4(g)$ is the total sum of a weight of the super absorbent polymer and a weight of the device capable of providing a load to the super absorbent polymer, after absorbing a physiological saline solution to the super absorbent polymer under a load (0.7 psi) for 1 hour.

As the super absorbent polymer prepared by the method of one embodiment exhibits the centrifuge retention capacity (CRC) and the absorbency under pressure (AUP) within the above-described range, the super absorbent polymer may have an EFFC of 24 to 28g/g, or 24.6 to 28g/g which is defined by the following formula 1.

$$EFFC = (CRC + AUP)/2 \quad \text{[Formula 1]}$$

in the formula 1,

CRC represents a centrifuge retention capacity for a physiological saline solution (0.9 wt % sodium chloride aqueous solution) of the super absorbent polymer for 30 minutes, and AUP represents an absorbency under pressure for a physiological saline solution (0.9 wt % sodium chloride aqueous solution) of the super absorbent polymer under 0.7 psi for 1 hour.

As described above, the super absorbent polymer can exhibit excellent absorption performance such as a basic absorption capacity and an absorbency under pressure.

In addition, the super absorbent polymer may have a saline flow conductivity (SFC) for a physiological saline solution of 30 to $160 \cdot 10^{-7} cm^3 \cdot s/g$, or 85 to $160 \cdot 10^{-7} cm^3 \cdot s/g$, or 85 to $120 \cdot 10^{-7} cm^3 \cdot s/g$. Thus, the super absorbent polymer can exhibit improved liquid permeability compared to previously known ones. This seems to be because predetermined silica particles and the like are contained in the surface cross-linked layer and the surface cross-linked layer having a certain level or more of thickness is uniformly formed.

This saline flow conductivity (SFC) can be measured and calculated according to the method well-known to those skilled in the art, for example, the method disclosed in column 16 [0184] to [0189] of U.S. Patent Application Publication No. 2009-0131255.

Further, the super absorbent polymer may have a gel strength (G') of 9,000 to 15,000 Pa, or 9,000 to 13,000 Pa, when measuring a horizontal gel strength of the super absorbent polymer using a rheometer, after absorbing and swelling a physiological saline solution (0.9 wt % sodium chloride aqueous solution) to the super absorbent polymer for 1 hour.

The horizontal gel strength G' can better reflect excellent liquid permeability under the environments of actually using water absorbent polymer. That is, conventionally the vertical gel strength of the super absorbent polymer can be determined to be highly relevant depending on whether to exhibit excellent shape retaining property and high gel strength, irrespective of the force provided in the horizontal direction when the super absorbent polymer was contained in the sanitary materials such as diapers. The horizontal gel strength can better reflect the gel strength directly related to such liquid permeability. Therefore, it has been found that the super absorbent polymer in which the horizontal gel strength G' satisfies the above-mentioned range exhibits excellent liquid permeability, and thus can be used very preferably for sanitary materials such as diapers.

This horizontal gel strength G' can be measured by a method comprising the following respective steps by using a commercialized rheometer, after a physiological saline has been absorbed to the super absorbent polymer for 1 hour.

1) a step of absorbing a physiological saline solution to the super absorbent polymer to swell the super absorbent polymer;

2) a step of positioning the swelled super absorbent polymer between plates of a rheometer having a predetermined interval to pressurize the two plate surfaces;

3) a step of confirming a shear strain in the linear viscoelastic regime section where storage modulus and loss modulus are steady, while increasing the shear strain using the rheometer under vibration; and 4) a step of measuring the storage modulus and the loss modulus of the swelled super absorbent polymer under the confirmed shear strain, respectively, and measuring the average value of the storage modulus as a gel strength.

As described above, the super absorbent polymer obtained according to the method of one embodiment maintains excellent absorption performance such as water retention capacity and absorbency under pressure and can satisfy more improved liquid permeability, gel strength and absorption rate. Accordingly, it can be suitably used for sanitary materials such as diapers, particularly, ultra-thin sanitary materials having reduced pulp content.

Advantageous Effects

According to the present invention, the super absorbent polymer which maintain excellent absorption performance such as a centrifuge retention capacity and an absorbency under pressure and exhibiting more improved liquid permeability, gel strength, absorption rate and the like can be prepared and provided.

This super absorbent polymer can be suitably used for sanitary materials such as disposable diapers, particularly ultra-thin sanitary materials with reduced content of pulp.

DETAILED DESCRIPTION OF THE EMBODIMENTS

Hereinafter, the preferred Examples are provided for better understanding of the invention. However, these Examples are given for illustrative purposes only and not intended to limit the scope of the present invention.

In the Examples and Comparative Examples below, the water-contact angles of hydrophobic silica particles and hydrophilic silica particles were measured as follows.

First, a coating solution in which the hydrophobic silica particles were dispersed in a methylene chloride solvent in the concentration of 5% by weight was used. After spin-coating the coating solution on a wafer, water was dropped dropwise onto the coating layer, and the contact angle was measured.

The contact angle thus measured is defined as a water-contact angle of the hydrophobic silica particles, and the measured values are shown in Table 1 below.

Further, in the case of hydrophilic silica particles, the water-contact angle was measured in the same manner as in the case of the hydrophobic silica particles, except that a coating liquid dispersed in water at a concentration of 20% by weight was used.

TABLE 1

| Silica particles | Product name | Water contact angle (°) |
| --- | --- | --- |
| Hydrophobic silica particles | Aerosil 200 | 14 |
| Hydrophilic silica particles | ST-O | 3 |

In the following Examples and Comparative Examples, the physical properties of each super absorbent polymer were measured and evaluated by the following methods.

(1) Evaluation of Particle Size

The particle sizes of the base polymer powder and the super absorbent polymer used in Examples and Comparative Examples were measured in accordance with EDANA (European Disposables and Nonwovens Association) recommended test method No. WSP 220.3.

(2) CRC (Centrifuge Retention Capacity)

For the absorbent polymer prepared in Examples and Comparative Examples, the centrifuge retention capacity (CRC) by absorption capacity under a non-loading condition was measured in accordance with EDANA (European Disposables and Nonwovens Association) recommended test method No. WSP 241.3.

That is, after uniformly inserting $W_{0(g)}$ (about 0.2 g) of each polymer obtained in Examples and Comparative Examples in a nonwoven fabric-made bag and sealing the same, it was soaked in a physiological saline solution composed of 0.9 wt % sodium chloride aqueous solution at room temperature. After 30 minutes, water was removed from the bag by centrifugation at 250 G for 3 minutes, and the weight $W_2(g)$ of the bag was then measured. Further, the same procedure was carried out without using the polymer, and then the resultant weight $W_1(g)$ was measured.

Using the respective weights thus obtained, the CRC(g/g) was determined according to the following calculation equation 1.

$$CRC(g/g)=\{[W_2(g)-W_1(g)-W_0(g)]/W_0(g)\} \quad \text{[Calculation Equation 1]}$$

in the calculation equation 1, $W_0(g)$ is an initial weight(g) of the super absorbent polymer, $W_1(g)$ is a weight of the device not including the super absorbent polymer, measured after soaking the same in a physiological saline solution for 30 minutes and dehydrating the same by using a centrifuge at 250 G for 3 minutes, and $W_2(g)$ is a weight of the device including the super absorbent polymer, measured after soaking the same in a physiological saline solution at room temperature for 30 minutes, and then dehydrating the same by using a centrifuge at 250 G for 3 minutes.

(3) Absorbency Under Pressure (AUP)

For the absorbent polymer prepared in Examples and Comparative Examples, the absorbency under pressure was measured in accordance with EDANA (European Disposables and Nonwovens Association) recommended test method No. WSP 242.3.

First, a 400 mesh stainless steel net was installed in the cylindrical bottom of a plastic having an internal diameter of 60 mm. $W_0$(g, 0.90 g) of the absorbent polymers prepared in Examples 1-6 and Comparative Examples 1-3 were uniformly scattered on the steel net under conditions of temperature of 23±2° C. and relative humidity of 45%, and a piston which can provide a load of 4.83 kPa (0.7 psi) uniformly was put thereon. The external diameter of the piston was slightly smaller than 60 mm, there was no gap between the cylindrical internal wall and the piston, and the jig-jog of the cylinder was not interrupted. At this time, the weight $W_3(g)$ of the device was measured.

After putting a glass filter having a diameter of 125 mm and a thickness of 5 mm in a Petri dish having a diameter of 150 mm, a physiological saline solution composed of 0.90 wt % of sodium chloride was poured in the dish until the surface level became equal to the upper surface of the glass filter. A sheet of filter paper having a diameter of 120 mm was put thereon. The measuring device was put on the filter paper and the solution was absorbed under a load for 1 hour. After 1 hour, the weight $W_4(g)$ was measured after lifting the measuring device up.

Using the respective mass fractions thus obtained, AUP (g/g) was calculated according to the following Calculation Equation 2, thereby confirming the absorbency under pressure.

$$AUP(g/g)=[W_4(g)-W_3(g)]/W_0(g) \quad \text{[Calculation Equation 2]}$$

in the calculation equation 2, $W_0(g)$ is an initial weight(g) of the super absorbent polymer, $W_3(g)$ is the total sum of a weight of the super absorbent polymer and a weight of the device capable of providing a load to the super absorbent polymer, and $W_4(g)$ is the total sum of a weight of the super absorbent polymer and a weight of the device capable of providing a load to the super absorbent polymer, after absorbing a physiological saline solution to the super absorbent polymer under a load (0.7 psi) for 1 hour.

(4) Saline Flow Conductivity (SFC)

The saline flow conductivity was measured in accordance with the method disclosed in Column 16 [0184] to [0189] of U.S. patent application publication no. 2009-0131255.

(5) Gel Strength (G')

For the absorbent polymers/based polymer powders prepared in Examples and Comparative Examples, the horizontal gel strength was measured.

First, the absorbent polymer samples (30~50 mesh) prepared in Examples and Comparative Examples were sieved off and 0.5 g of the samples were weighed. The weighed samples were sufficiently swelled in 50 g of a physiological saline solution for 1 hour. After that, the solvent not absorbed therein was removed by using an aspirator for 4 minutes, and the solvent left on the surface of the same was evenly distributed and wiped once with a filter paper.

2.5 g of the swelled super absorbent polymer was loaded between two parallel plates (parallel plates with a 25 mm diameter, a lower plate thereof having a wall with a 2 mm height for preventing the sample from leaking) of the rheometer, and the gap (1 mm) between the parallel plates was adjusted. At this time, the gap between the parallel plates was properly adjusted by pressing the plates with a force of about 3 N so that the swelled sample contacted evenly at the face of the plates.

A linear viscoelastic regime section of strain where the storage modulus and the loss modulus were steady was found by using the rheometer while increasing the shear strain at a 10 rad/s oscillation frequency. Generally, in the case of a swelled super absorbent polymer, a strain of 0.1% is imparted in the liner viscoelastic regime section.

The storage modulus and the loss modulus of the swelled super absorbent polymer was measured by using the strain value of the linear viscoelastic regime section at an oscillation frequency of 10 rad/s for 60 seconds. The horizontal gel strength was obtained by taking an average of the obtained storage modulus. For reference, the loss modulus was measured as a very small value as compared to the storage modulus.

EXAMPLE 1

In a 2 L capacity glass reactor surrounded by a jacket in which a heating medium cooled beforehand to 25° C. was circulated, 500 g of acrylic acid, 2 g of internal crosslinking agent polyethylene glycol diacrylate (PEGDA; Mw=500) and 0.25 g of allylacrylate were injected, and the initiator of IRGACURE 819 was injected in the content of 100 ppmw based on the total acrylic acid.

Subsequently, 720 g of a 24 wt % caustic soda (NaOH) aqueous solution was slowly added dropwise to the glass reactor. During dropwise addition of the caustic soda solution, it was waited until the temperature of the monomer composition was increased up to about 72° C. due to neutralization heat, and then cooled down to about 45° C. Thereafter, it was confirmed that the neutralization ratio of acrylic acid in the monomer composition thus obtained was about 70 mol %.

After the temperature of the monomer composition was cooled to about 45° C., 28 g of sodium bicarbonate solution (diluted to 4% by weight in water) prepared beforehand was injected and mixed.

Then, the above monomer composition was irradiated with light for 1 minute, and the temperature of the glass reactor was raised to 75° C. to carry out the polymerization reaction. The polymer obtained through the polymerization reaction was passed through a hole having a diameter of about 13 mm using a meat chopper to produce a coarsely pulverized polymer in a crump state.

Subsequently, the polymer in the crump state was dried in an oven capable of shifting airflow upward and downward. The polymer in the crump state was uniformly dried by flowing hot air at 180° C. from the bottom to the top for 15 minutes and again from the top to the bottom for 15 minutes, and the water content of the finally dried polymer as adjusted to be 2% or less.

The dried polymer was pulverized using a pulverizing device and classified to obtain a base polymer powder having a particle size of 150 μm to 850 μm.

Based on 100 g of the base polymer powder, a surface treatment liquid containing 0.04 g of hydrophobic silica particles (Aerosil 200), 0.04 g of hydrophilic silica particles (ST-O), 1.5 g of ethylene carbonate, 0.05 g of polycarboxylic acid-based copolymer disclosed in Preparation Example 1 of Korean Patent Laid-open Publication No. 2015-0143167 (Korean Patent Application No. 2014-0072343), and 4.0 g of water as a solvent was formed. This surface crosslinking liquid was sprayed onto the base polymer powder, stirred at room temperature, and mixed so that the surface treatment liquid was evenly distributed on the base polymer powder. Thereafter, the base polymer powder was placed in a surface crosslinking reactor to carry out the surface crosslinking reaction.

In the surface crosslinking reactor, it was confirmed that the base polymer powder was gradually heated at an initial temperature near 180° C. After 30 minutes elapsed, operation was performed so as to reach the maximum reaction temperature of 190° C. After reaching the maximum reaction temperature, additional reaction was carried out for 65 minutes, and a sample of the finally produced super absorbent polymer was taken. After the surface crosslinking step, a surface-crosslinked super absorbent polymer having a particle size of about 150 to 850 mm was obtained by using a sieve.

EXAMPLE 2

A surface cross-linked super absorbent polymer was prepared in the same manner as in Example 1, except that, based on 100 g of the base polymer powder obtained by the same method as in Example 1, a surface treatment liquid containing 0.02 g of hydrophobic silica particles (Aerosil) 200, 0.02 g of hydrophilic silica particles (ST-O), 1.5 g of ethylene carbonate, 0.05 g of polycarboxylic acid-based copolymer disclosed in Preparation Example 1 of Korean Patent Laid-open Publication No. 2015-0143167 (Korean Patent Application No. 2014-0072343), and 4.0 g of water as a solvent was formed and used.

After the above surface crosslinking step, a surface cross-linked super absorbent polymer having a particle size of about 150 to 850 μm was obtained by using a sieve.

EXAMPLE 3

A surface cross-linked super absorbent polymer was prepared in the same manner as in Example 1, except that, based on 100 g of the base polymer powder obtained by the same method as in Example 1, a surface treatment liquid containing 0.03 g of hydrophobic silica particles (Aerosil 200), 0.03 g of hydrophilic silica particles (ST-O), 1.5 g of ethylene carbonate, 0.05 g of polycarboxylic acid-based copolymer disclosed in Preparation Example 1 of Korean Patent Laid-open Publication No. 2015-0143167 (Korean Patent Application No. 2014-0072343), and 4.0 g of water as a solvent was formed and used.

After the above surface crosslinking step, a surface cross-linked super absorbent polymer having a particle size of about 150 to 850 µm was obtained by using a sieve.

EXAMPLE 4

A surface cross-linked super absorbent polymer was prepared in the same manner as in Example 1, except that, based on 100 g of the base polymer powder obtained by the same method as in Example 1, a surface treatment liquid containing 0.02 g of hydrophobic silica particles (Aerosil 200), 0.04 g of hydrophilic silica particles (ST-O), 1.5 g of ethylene carbonate, 0.05 g of polycarboxylic acid-based copolymer disclosed in Preparation Example 1 of Korean Patent Laid-open Publication No. 2015-0143167 (Korean Patent Application No. 2014-0072343), and 4.0 g of water as a solvent was formed and used.

After the above surface crosslinking step, a surface cross-linked super absorbent polymer having a particle size of about 150 to 850 µm was obtained by using a sieve.

EXAMPLE 5

A surface cross-linked super absorbent polymer was prepared in the same manner as in Example 1, except that, based on 100 g of the base polymer powder obtained by the same method as in Example 1, a surface treatment liquid containing 0.02 g of hydrophobic silica particles (Aerosil 200), 0.06 g of hydrophilic silica particles (ST-O), 1.5 g of ethylene carbonate, 0.05 g of polycarboxylic acid-based copolymer disclosed in Preparation Example 1 of Korean Patent Laid-open Publication No. 2015-0143167 (Korean Patent Application No. 2014-0072343), and 4.0 g of water as a solvent was formed and used.

After the above surface crosslinking step, a surface cross-linked super absorbent polymer having a particle size of about 150 to 850 µm was obtained by using a sieve.

EXAMPLE 6

A surface cross-linked super absorbent polymer was prepared in the same manner as in Example 1, except that, based on 100 g of the base polymer powder obtained by the same method as in Example 1, a surface treatment liquid containing 0.04 g of hydrophobic silica particles (Aerosil 200), 0.02 g of hydrophilic silica particles (ST-O), 1.5 g of ethylene carbonate, 0.05 g of polycarboxylic acid-based copolymer disclosed in Preparation Example 1 of Korean Patent Laid-open Publication No. 2015-0143167 (Korean Patent Application No. 2014-0072343), and 4.0 g of water as a solvent was formed and used.

After the above surface crosslinking step, a surface cross-linked super absorbent polymer having a particle size of about 150 to 850 µm was obtained by using a sieve.

EXAMPLE 7

A surface cross-linked super absorbent polymer was prepared in the same manner as in Example 1, except that, based on 100 g of the base polymer powder obtained by the same method as in Example 1, a surface treatment liquid containing 0.04 g of hydrophobic silica particles (Aerosil 200), 0.02 g of hydrophilic silica particles (ST-O), 1.5 g of ethylene carbonate, 0.05 g of polycarboxylic acid-based copolymer disclosed in Preparation Example 1 of Korean Patent Laid-open Publication No. 2015-0143167 (Korean Patent Application No. 2014-0072343), and 4.0 g of water as a solvent was formed and used.

After the above surface crosslinking step, a surface cross-linked super absorbent polymer having a particle size of about 150 to 850 µm was obtained by using a sieve.

Comparative Example 1

A surface cross-linked super absorbent polymer was prepared in the same manner as in Example 1, except that, based on 100 g of the base polymer powder obtained by the same method as in Example 1, a surface treatment liquid containing 1.5 g of ethylene carbonate, 0.05 g of polycarboxylic acid-based copolymer disclosed in Preparation Example 1 of Korean Patent Laid-open Publication No. 2015-0143167 (Korean Patent Application No. 2014-0072343), and 4.0 g of water as a solvent was formed and used.

After the above surface crosslinking step, a surface cross-linked super absorbent polymer having a particle size of about 150 to 850 µm was obtained by using a sieve.

Comparative Example 2

A surface cross-linked super absorbent polymer was prepared in the same manner as in Example 1, except that, based on 100 g of the base polymer powder obtained by the same method as in Example 1, a surface treatment liquid containing 0.06 g of hydrophobic silica particles (Aerosil 200), 1.5 g of ethylene carbonate, and 4.0 g of water as a solvent was formed and used.

After the above surface crosslinking step, a surface cross-linked super absorbent polymer having a particle size of about 150 to 850 µm was obtained by using a sieve.

For the super absorbent polymers of Examples 1 to 7 and Comparative Examples 1 to 2, the physical property measurement and evaluation of CRC, AUP, SFC and gel strength were carried out, and the measured physical property values are shown in Table 2 below. In addition, from the measured CRC and AUP, the EFFC values of the formula 1 were calculated and shown in Table 2 below.

TABLE 2

|  | CRC (g/g) | AUP (g/g) | EFFC (g/g) | SFC ($10^{-7} cm^3 \cdot s/g$) | Gel strength (Pa) |
| --- | --- | --- | --- | --- | --- |
| Example 1 | 29.3 | 22.0 | 25.7 | 89 | 9158 |
| Example 2 | 28.1 | 22.2 | 25.1 | 91 | 9437 |
| Example 3 | 27.8 | 21.4 | 24.6 | 115 | 12365 |
| Example 4 | 28 | 22.0 | 25 | 93 | 9957 |
| Example 5 | 28.1 | 21.5 | 24.8 | 97 | 10588 |
| Example 6 | 28.1 | 21.7 | 24.9 | 99 | 11268 |
| Example 7 | 28 | 21.6 | 24.8 | 99 | 11302 |
| Comparative Example 1 | 28.1 | 22.3 | 25.2 | 61 | 6935 |
| Comparative Example 2 | 28.8 | 21.3 | 25.1 | 82 | 7186 |

Referring to Table 2, it was confirmed that the super absorbent polymers of Examples 1 to 7 exhibited absorption characteristics (CRC, AUP, and EFFC) in a level equal to or higher than those of Comparative Examples, and more improved gel strength and liquid permeability.

The invention claimed is:
1. A super absorbent polymer comprising:
a base polymer powder including a first cross-linked polymer polymerized from a water-soluble ethylenically unsaturated monomer having at least partially neutralized acidic groups;

a surface cross-linked layer including a second cross-linked polymer formed on the base polymer powder, the second cross-linked polymer formed by further cross-linking the first cross-linked polymer using a surface crosslinking agent; and a hydrophilic silica particle and having a water-contact angle of more than 1° and 10° or less, hydrophobic silica particles having a water-contact angle of more than 12° and 150° or less, and a polycarboxylic acid-based copolymer where the hydrophilic and hydrophobic particles, and the polycarboxylic acid-based copolymer are dispersed in the surface cross-linked layer, wherein the super absorbent polymer has:

a EFFC represented by the following formula 1 of 24 to 28 g/g, a saline flow conductivity (SFC) of 85 to 160 ($\cdot 10^{-7}$ cm$^3$·s/g), the SFC measured using a physiological saline solution of 0.685 wt % sodium chloride aqueous solution, and a gel strength (G') of 9,000 to 15,000 Pa, wherein G' is a horizontal gel strength of the super absorbent polymer measured using a rheometer, after absorbing and swelling the super absorbent polymer for 1 hour using a physiological saline solution of 0.9 wt % sodium chloride aqueous solution, $$EFFC=(CRC+AUP)/2 \quad\quad \text{[Formula 1]}$$

in Formula 1, the centrifuge retention capacity (CRC) of the superabsorbent polymer is measured for 30 minutes using a physiological saline solution of 0.9 wt % sodium chloride aqueous solution, and the absorbency under pressure (AUP) of the superabsorbent polymer is measured under a load of 0.7 psi for 1 hour using a physiological saline solution of 0.9 wt % sodium chloride aqueous solution.

2. The super absorbent polymer of claim 1, wherein the hydrophilic silica particles or the hydrophobic silica particles are dispersed in the surface cross-linked layer, or are embedded in the surface of the surface cross-linked layer.

3. The super absorbent polymer of claim 1, wherein the hydrophilic silica particle have a water-contact angle of more than 1° and 3° or less, and wherein the hydrophobic silica particles have a water-contact angle of 14° or more and 150° or less.

4. A method for preparing the superabsorbent polymer of claim 1, the method comprising the steps of:

carrying out a crosslinking polymerization of the water-soluble ethylenically unsaturated monomer having at least partially neutralized acidic groups in the presence of an internal crosslinking agent to form a hydrogel polymer including the cross-linked polymer;

drying, pulverizing, and classifying the hydrogel polymer to form the base polymer powder; and surface-crosslinking the base polymer powder by using a surface crosslinking liquid containing a surface crosslinking agent of an alkylene carbonate having 2 to 5 carbon atoms, in the presence of the hydrophobic silica particles having a water-contact angle of more than 12° and 150° or less, and the hydrophilic silica particles having a water-contact angle of more than 1° and 10° or less.

5. The method for preparing a super absorbent polymer of claim 4, wherein the surface crosslinking step comprises subjecting the base polymer powder to heat treatment in the presence of the hydrophobic silica particles, the hydrophilic silica particles, and the surface crosslinking liquid containing the surface crosslinking agent to carry out a surface crosslinking the surface.

6. The method for preparing a super absorbent polymer of claim 5, wherein the hydrophobic silica particles have a water-contact angle of 50° to 150° and the surface crosslinking liquid further includes a dispersant.

7. The method for preparing a super absorbent polymer of claim 4, wherein the hydrophobic silica particles and the hydrophilic silica particles are used in the content of 0.0001 to 0.3 parts by weight based on 100 parts by weight of the base polymer powder, respectively.

8. The method for preparing a super absorbent polymer of claim 4, wherein the water-soluble ethylenically unsaturated monomer includes at least one selected from the group consisting of anionic monomers of acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid or 2-(meth)acrylamido-2-methylpropanesulfonic acid, and their salts; non-ionic, hydrophilic group-containing monomers of (meth)acrylamide, N-substituted (meth)acrylate, 2-hydroxyethyl(meth)acrylate, 2-hydroxypropyl(meth)acrylate, methoxypolyethylene glycol(meth)acrylate or polyethylene glycol (meth)acrylate; and amino group-containing unsaturated monomers of (N,N)-dimethylaminoethyl(meth)acrylate or (N,N)-dimethylaminopropyl(meth)acrylamide, and their quaternary product.

9. The method for preparing a super absorbent polymer of claim 4, wherein the internal crosslinking agent includes at least one selected from the group consisting of bis(meth)acrylamide having 8 to 12 carbon atoms, poly(meth)acrylate of polyol having 2 to 10 carbon atoms and poly(meth)acrylate having 2 to 10 carbon atoms.

10. The method for preparing a super absorbent polymer of claim 4, wherein the base polymer powder is pulverized and classified to have a particle size of 150 to 850 µm.

11. The method for preparing a super absorbent polymer of claim 4, wherein the surface crosslinking step is carried out by subjecting to a heat treatment under the condition in which the temperature is raised from an initial temperature of 20° C. to 130° C. to a maximum temperature of 140° C. to 200° C. for 10 minutes to 40 minutes, and the maximum temperature is maintained for 5 minutes to 80 minutes.

* * * * *